(12) United States Patent
Caserta et al.

(10) Patent No.: US 7,106,956 B2
(45) Date of Patent: Sep. 12, 2006

(54) ELECTRICAL DEVICE FOR THE RELEASE OF ACTIVE SUBSTANCES

(75) Inventors: Andrea Caserta, Barcelona (ES); Julio Cesar Ruiz Ballesteros, Barcelona (ES); Cedric Morhain, Barcelona (ES)

(73) Assignee: Zobele España, S.A., Barcelona (ES)

( * ) Notice: Subject to any disclaimer, the term of this patent is extended or adjusted under 35 U.S.C. 154(b) by 0 days.

(21) Appl. No.: 10/527,644

(22) PCT Filed: Mar. 12, 2003

(86) PCT No.: PCT/ES03/00112

§ 371 (c)(1),
(2), (4) Date: Mar. 14, 2005

(87) PCT Pub. No.: WO2004/080496

PCT Pub. Date: Sep. 23, 2004

(65) Prior Publication Data

US 2005/0249673 A1    Nov. 10, 2005

(51) Int. Cl.
*F24F 6/00* (2006.01)

(52) U.S. Cl. ...................................... 392/394; 392/395

(58) Field of Classification Search ................ 392/386, 392/390, 391, 392, 394, 395; 239/34, 43, 239/44, 45, 46; 122/366
See application file for complete search history.

(56) References Cited

U.S. PATENT DOCUMENTS 5,945,094 A * 8/1999 Martin et al. ............... 424/76.1
6,775,470 B1 * 8/2004 Zobele et al. ............... 392/390

FOREIGN PATENT DOCUMENTS

| DE | 41 31 613 A1 | 3/1993 |
|---|---|---|
| EP | 0 722 742 A2 | 7/1996 |
| EP | 1 240 907 A1 | 9/2002 |
| EP | 1 270 021 A1 | 1/2003 |
| WO | WO 98/46285 | 10/1998 |

OTHER PUBLICATIONS

International Search Report dated May 19, 2003, in PCT/ES2003/00112.

* cited by examiner

*Primary Examiner*—Sang Paik
(74) *Attorney, Agent, or Firm*—McDermott Will & Emery LLP

(57) ABSTRACT

The device comprises conventionally a plug (2) for the electrical supply of a heater element (14) to bring about the heating and evaporation, by way of a flat wick (10), of an active substance contained in a main receptacle (5). The novelty lies in the fact that said container (5) is heat-formed and defines a triangular configuration reservoir (6) with a flat extension (7) that accommodates the flat "Y"-shaped wick (10) in which the ends of its divergent arms (11) are engaged in recesses (9) in the mouth of the active substance reservoir (6), said wick (10) being pressed by an impermeable strip (12) which is heat-sealed to the body of the reservoir (6), so that the heater element (14) positioned facing the front end of the extension (7) brings about the warming of the wick (10) and the corresponding evaporation of the active substance, which will issue by way of a hole (16) in the impermeable strip (12) to be diffused in the environment. In the plug-in position the device remains with the container (5) of the wick (10) in the vertical position, and in direct contact of this with the active substance contained in the reservoir (6).

11 Claims, 4 Drawing Sheets

ELECTRICAL DEVICE FOR THE RELEASE OF ACTIVE SUBSTANCES

OBJECT OF THE INVENTION

The present invention refers to an electrical device for releasing active substances, which is evidently intended for the diffusion to the ambientals of an active substance contained in a receptacle from which, by means of a wick by capillarity, the active substance reaches an area where there is a heating element situated with which evaporation is achieved and therefore the diffusion to the exterior of the active substance, all of this making up a device on which a plug is provided for the supply of the heating element supply current.

BACKGROUND OF THE INVENTION

The technology, which consists of making use of a porous wick to supply an area where there is a heating means for the evaporation of the active substance stored in a container, is already known, as are commercial appliances or devices for diffusing active substances by means of a cylindrical wick contained in a bottle produced by means of blown injection and wherein the cylindrical wick which protrudes to the exterior of the bottle is warmed with an electrically-operated heating element, bringing about the heating, evaporation and, therefore, the diffusion of the active substance to the environment.

Appliances and devices of this type are used for releasing not only aromatic active substances to the environment, but also for releasing active substances intended to be used as repellents or as compounds for eliminating insects, etc.

To be specific, we may mention appliances described in patents held by the same applicant, such as WO 02/28442; WO 98/58692; EP 0689766 A1 and WO 98/57674.

In all those documents the wick in contact with the active substance has a cylindrical configuration, which means that the heater also has to have a cylindrical geometry.

However, the patent now abandoned EP 0722742 A2 describes a device of the type referred to wherein the wick is flat and is associated with a heat-formed container, though with limitations as regards efficacy of evaporation and a complication in respect of the final sealing of the product, as it is done on two different surfaces, so in practice sealing is assured by the use of two heat-formed receptacles, one inside the other.

DESCRIPTION OF THE INVENTION

The device advocated, being of the type of those referred to above, i.e. having a plug for the electrical supply and fitted with a heating element, as well as a heat-formed container and a flat wick that conveys the liquid from the container to the portion of said wick that protrudes to the exterior thereof, has the special feature that the heat-formed container is made up of two parts, one determining the bottle for the active substance and the other flat and stemming from the previous one for positioning the flat wick, which is located in a recess established for the purpose in that flat part and emerging from the container, retained and sealed by means of an impermeable strip that not only covers the wick in its entirety, but also seals the active substance container, in such a way that this impermeable strip is provided with a hole for the output of the active substance which is produced by the evaporation of same when the area corresponding to the flat portion of the device is warmed by means of the energizing of the respective heater.

The configuration of the active substance container is triangular and the surface on which the impermeable strip rests presents two positioning notches, one for each of the ends of the wings belonging to the flat wick, as this has the special feature of having a "Y" configuration, so that the straight arm is positioned as stated above, while the divergent arms protrude so that their ends are positioned in those recesses or notches established in the body of the container, all this so that irrespective of the position in which the appliance is connected to a plug, whether horizontal or vertical, providing that at least one of the arms of the wick is in contact with the active substance. In addition, in the position of use, whether plugged in horizontally or vertically, the container is in the vertical position, as is the wick. Obviously, any alternative wick geometry may be considered with a central portion corresponding to the warming/evaporation area and a bottom portion presenting a planar symmetry in respect of this central axis for the purpose of supplying the central portion with liquid in the two positions of use, whether horizontally or vertically.

To prevent leakage during the storage of the device, a seal or impermeable label is provided which is applied on the area of the hole corresponding to the impermeable strip sealing the container, whose seal or label has to be separated before initial use. In comparison with the device described in patent EP 0722742 A2, the proper leaktightness of the container is assured as said seal is applied on a single strip.

Furthermore, provision is also made for the heater to be able to be protected in an inner housing, which would be fitted as a safety means so that, in case the user should handle the device in its plugged-in position, he cannot reach or come into contact with said heater and therefore prevents the hazard that could be represented by an electric shock.

The plug is also designed to be rotary, in which case it is not necessary for the wick to be "Y" shaped, as the plug only has to be turned for the container to be in the desired position.

It is also planned for the device to be embodied with the container, its wick and the sealing label, in rotary fashion in respect of the housing, which would also enable the container to be situated always in the desired position, irrespective of the way the plug-in position is achieved.

In another possible embodiment it is planned that the container could be exchangeable, since, although it is designed to form part of a disposable device, it should be changed and replaced with another, just by making one portion of the body or main housing operable so as to be able to gain access to this container and carry out its replacement.

DESCRIPTION OF THE DRAWINGS

To supplement the description that is going to be given below and in order to assist a clearer understanding of the features of the invention, in accordance with a preferred example of a practical embodiment of same, the present description is accompanied by a set of drawings wherein for informative but never restrictive purposes the following is represented.

PREFERRED EMBODIMENT OF THE INVENTION

Figure 1:
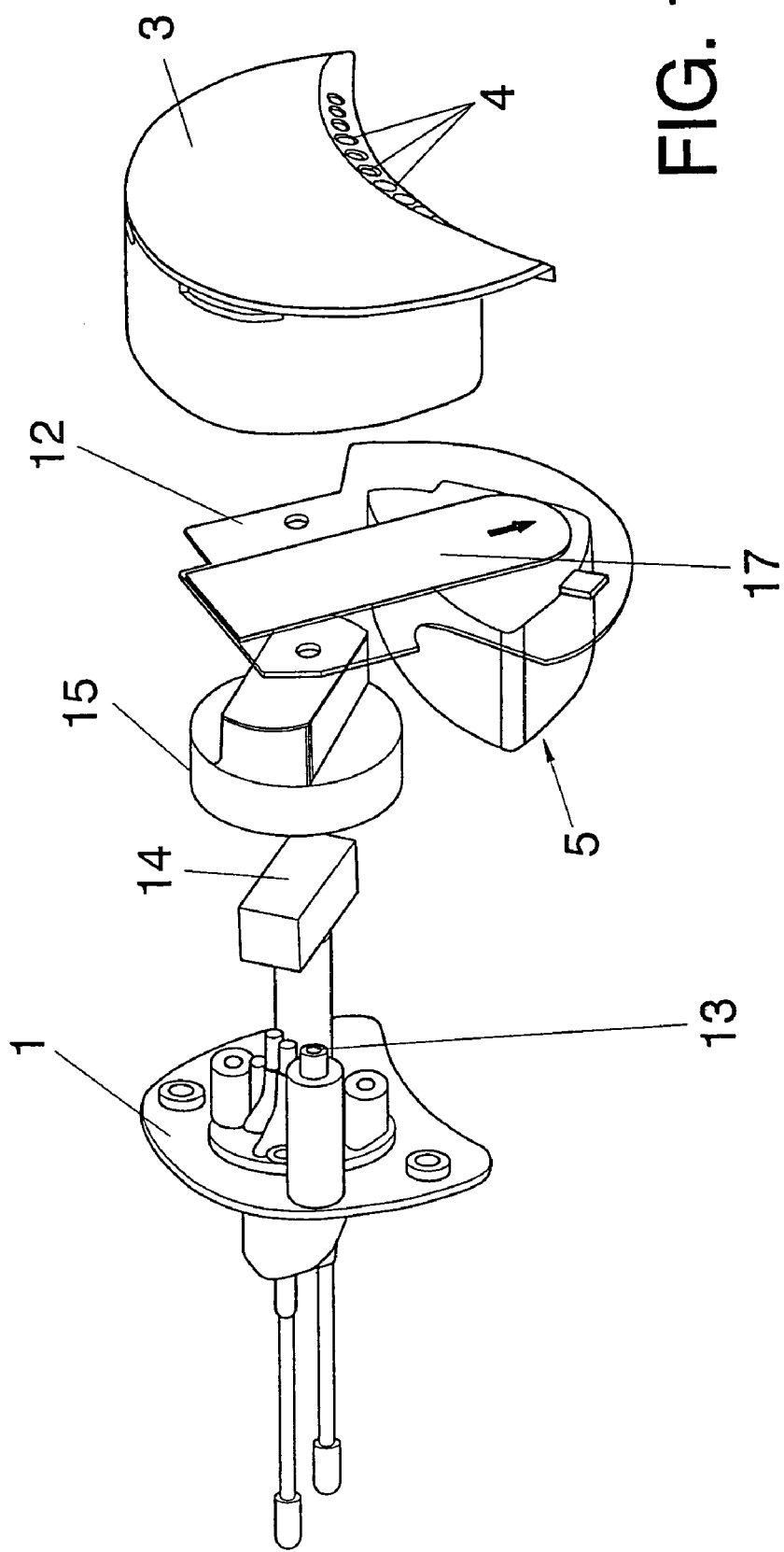
FIG. 1.—It shows a representation according to an exploded perspective of the different parts and components of the active substance releasing device made according to the object of the present invention.

In the light of the above-mentioned figures, it may be seen that the device of the invention comprises a body (1) which is prolonged on one side in the plug (2) for electric current supply, while on the other side it is integral with a housing (3) forming a one-piece body. Said housing (3) has holes or openings (4) for the circulation of air in the area of the wick so as to facilitate the discharge of the active substance vaporized or released as will be explained later.

The device has a heat-formed container for the active substance, referenced in general with number (5) and which comprises a small reservoir (6) of triangular configuration with a flat extension (7) matching up with one of its bases, specifically with the open base, which is sealed by means of an impermeable strip (12) attached by heat on the surface of the container body (6) and its flat extension (7), in order to form the body of the heat-formed container in this way, as stated above. This flat configuration (7) is provided with a recess (8), while the reservoir or container (6) presents a pair of notches (9), in order that in the positioning of the respective wick (10), which is flat, a straight portion of this is positioned in the recess (8), while the ends of the divergent wings (11), which form a "Y" configuration with the straight portion, are each positioned in the above-mentioned notches (9), so that said wick (10) is pressed between both parts, i.e. between the body (6) of the container with its flat surface (7) and the impermeable strip (12), which is attached to it be heat-sealing.

The main body (5) of the container is assembled on the body (1) of the device by inserting projections (13) from said body (1) into holes (14) made for the purpose in the body (5) of the container.

A heater element (14), as is conventional, naturally connected to the plug (2), will be faced up against the flat portion (7) of the body of the container (5), so that, when this heater (14) is energized, the wick (10) situated in this flat portion is warmed and whereby the active substance which is conveyed by capillarity from the actual reservoir (6) to the end portion of the aforesaid wick (10) is evaporated.

The heater element (14) may be supplemented with a protection and safety housing (15), while on the impermeable strip (12) and covering a hole (16) in it by way of which the evaporated substance will be released, a sealing label or strip (17) will be provided for removal at the time the device is first used.

When the device is plugged in, whether with the plug vertical or horizontal, the body or container (5) and the actual wick (10) will always be in the vertical position, and depending on whether the plug is horizontal or vertical, the reservoir (6) will either be in a lateral oblique disposition or in a centred vertical disposition, but in either of the positions the wick (10) will always remain in contact with the active substance contained in the reservoir (6) as a result of the ends (11) of the legs or arms of the "Y" configuration of said wick (10) being located on the notches (9) of the aforesaid container reservoir (6).

Figure 2:
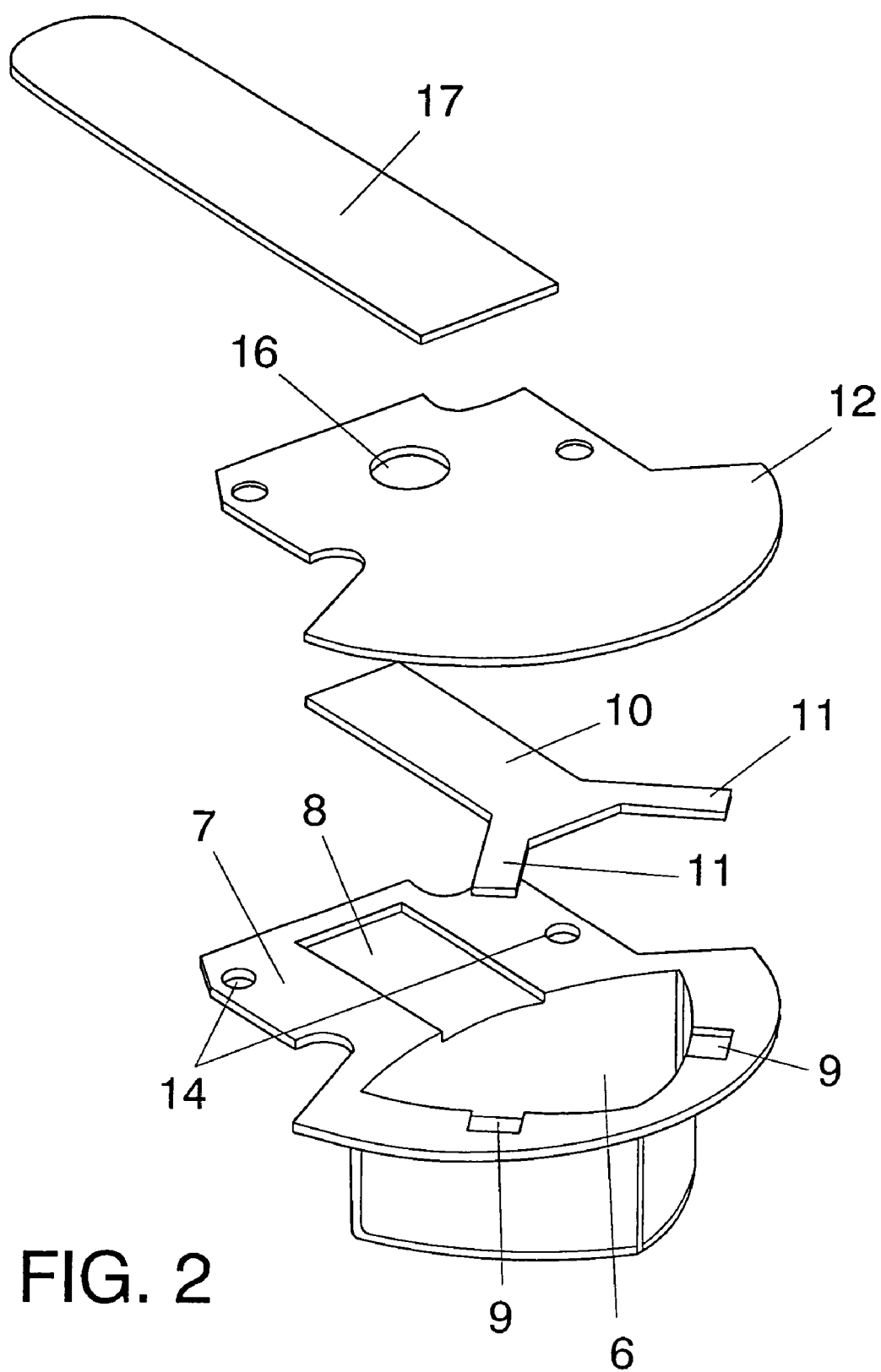
FIG. 2.—It shows an exploded view of the different parts and components making up the container unit for releasing the active substance.
Figure 3:
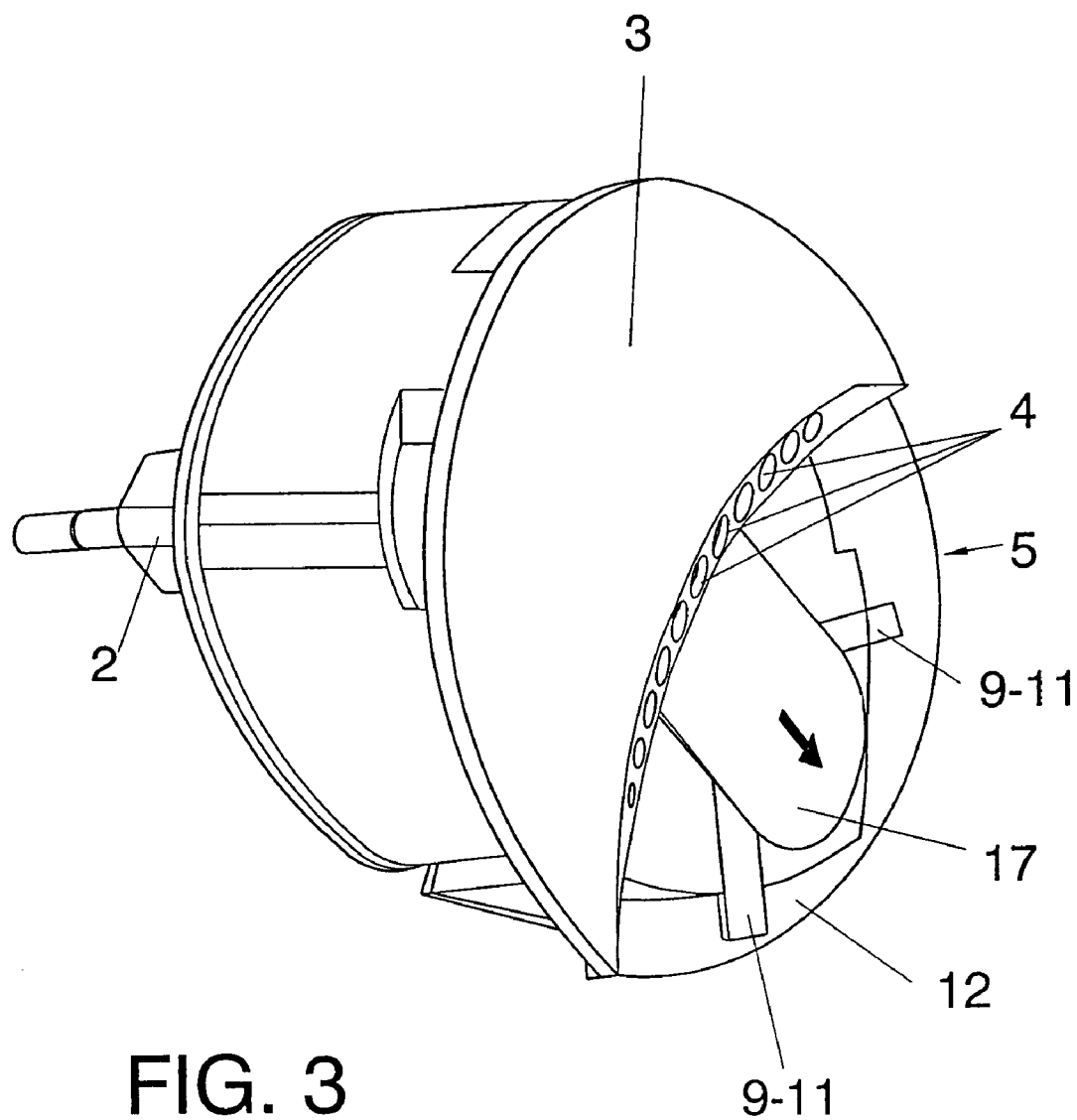
FIG. 3.—It shows a perspective view of the device produced by assembling the parts represented in FIG. 1.
Figure 4:
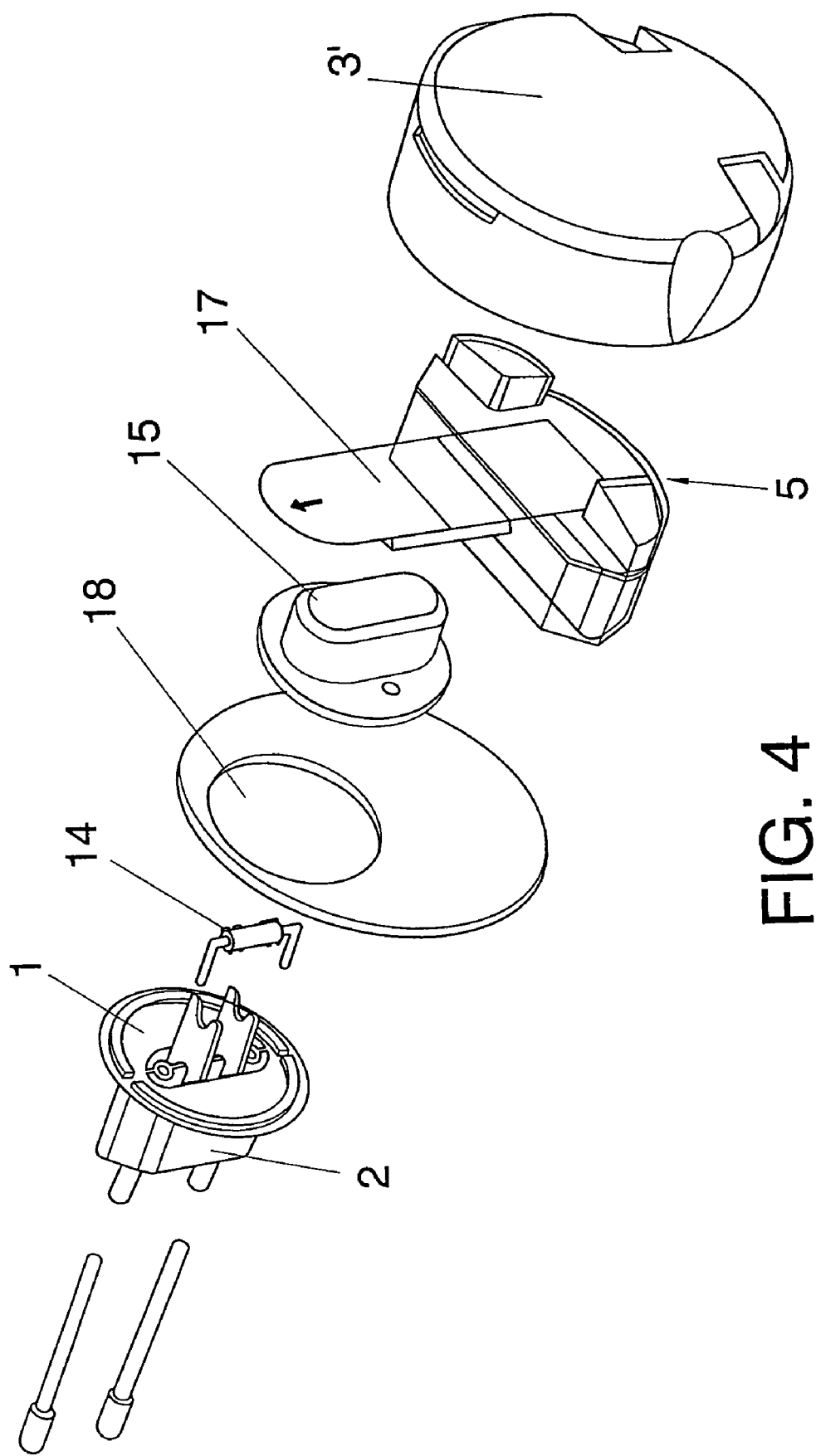
FIG. 4.—Lastly, it shows an arrangement of the parts and components making up the device in an alternative embodiment in which the plug is rotary in respect of the rest of the device.

As shown in FIG. 4, the plug (2) may be fitted in rotary fashion, so that in this case the body (1) is housed in a hole (18) of a support plate, and the container unit (5) mounted on the housing (3') but released in respect of the support body (1), in order that the plug to which that body (1) body belongs may turn in relation to the container (5) and thereby be able to vary the position of the latter, irrespective of the position of the plug (2) on the respective socket outlet, so the wick (10) may be completely straight instead of having the "Y" configuration represented in FIGS. 1 and 2. In this case, the form of embodiment represented in FIG. 4, the heater element (4) may also be protected with a housing (15) as in the above case.

It is also envisaged that the housing (3) or (3') of the device may be operable, i.e. be attached to the body (1), either in a hinged or separable way, to facilitate the replaceability of the heat-formed container (5) and be able to carry out its replacement instead of its being disposed of once the active substance is used up, which is what the device of the invention is primarily designed for.

Amongst the advantages of the device, we may single out as the most important the following:

Simplicity of structure and use.
Low cost of materials.
Easy assembly of the different parts.
Optimal wick utilisation.
Possibility of marketing as a disposable active substance releasing device.
Possibility of replacing the reservoir unit containing active substance with the wick.

Finally, it should be mentioned that there is a possibility that the assembly of the heat-formed container body (5) may have the vaporized substance output hole (16) opposite the heater (14), thereby enhancing the chimney effect.

The invention claimed is:

1. An electric device for releasing active substances, comprising:
   a support body;
   an external plug stemming from said support body for connecting the device to a main supply;
   a flat wick comprising a first arm and two divergent arms which extend from said first arm;
   a heater element situated close to said flat wick;
   a heat-formed container comprising a reservoir, said flat wick being arranged to convey an active substance by capillarity from the reservoir up to an area of said flat wick which protrudes out of the reservoir of said heat-formed container and which is located close to said heater element, wherein the reservoir has a noticeably triangular configuration and a flat extension with a depression housing said first arm of said flat wick, which is pressed between a surface of the flat extension and an impermeable strip, which is thermowelded to said heat-formed container,
   wherein said two divergent arms of said flat wick extend from said first arm into the reservoir in a manner such that if said external plug is vertically oriented, a first one of said two divergent arms is substantially vertically oriented so as to guarantee contact with the active substance, and if said external plug is horizontally oriented, a second one of said two divergent arms is substantially vertically oriented so as to guarantee contact with the active substance.

2. The electric device for releasing active substances according to claim 1, wherein said flat wick is a Y-shaped wick.

3. The electric device for releasing active substances according to claim 1, wherein said first arm of said flat wick is positioned in the depression provided in the flat extension while an end of each divergent arm is located in a corresponding groove provided in a corresponding edge of the reservoir.

4. The electric device for releasing active substances according to claim 3, wherein the impermeable strip, which seals the reservoir and is also attached to the flat extension, is provided with a hole for the output of vapors caused by said heater element warming the active substance, said heater element facing the flat extension where said flat wick is situated.

5. The electric device for releasing active substances according to claim 4, wherein the hole is plugged by a sealing strip arranged to be removed when the device is going to be used for the first time so as to prevent leakage of the active substance during storage and handling of the device.

6. The electric device for releasing active substances according to claim 3, wherein said external plug is not rotatable with respect to said heat-formed container.

7. The electric device for releasing active substances according to claim 1, wherein the impermeable strip, which seals the reservoir and is also attached to the flat extension, is provided with a hole for the output of vapors caused by said heater element warming the active substance, said heater element facing the flat extension where said flat wick is situated.

8. The electric device for releasing active substances according to claim 7, wherein the hole is plugged by a sealing strip arranged to be removed when the device is going to be used for the first time so as to prevent leakage of the active substance during storage and handling of the device.

9. The electric device for releasing active substances according to claim 1, wherein said heater element is supplemented with an inner safety housing.

10. The electric device for releasing active substances according to claim 1, wherein said external plug is not rotatable with respect to said heat-formed container.

11. The electric device for releasing active substances according to claim 1, further comprising a housing attached to said support body, said housing arranged to permit access to or exchangeability of said heat-formed container.

* * * * *